(12) United States Patent
Richter (10) Patent No.: US 6,770,092 B2
(45) Date of Patent: Aug. 3, 2004

(54) METHOD OF DELIVERING A BIFURCATED STENT

(75) Inventor: Jacob Richter, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 0 days.

(21) Appl. No.: 10/228,099

(22) Filed: Aug. 27, 2002

(65) Prior Publication Data

US 2003/0074047 A1 Apr. 17, 2003

Related U.S. Application Data

(60) Continuation-in-part of application No. 09/891,767, filed on Jun. 26, 2001, now Pat. No. 6,540,779, which is a continuation of application No. 09/072,846, filed on May 5, 1998, now Pat. No. 6,251,133, which is a continuation of application No. 09/049,842, filed on Mar. 27, 1998, now Pat. No. 6,090,133, which is a continuation of application No. 08/911,606, filed on Aug. 14, 1997, now Pat. No. 5,827,320, which is a continuation of application No. 08/841,702, filed on Apr. 30, 1997, now Pat. No. 5,755,735, which is a continuation of application No. 08/840,612, filed on Apr. 29, 1997, now Pat. No. 5,755,734, which is a division of application No. 08/642,297, filed on May 3, 1996, now abandoned, application No. 10/228,099, which is a continuation-in-part of application No. 10/066,755, filed on Feb. 6, 2002, which is a division of application No. 09/575,957, filed on May 23, 2000, now Pat. No. 6,440,165.

(51) Int. Cl.[7] .................................................. A61F 2/06
(52) U.S. Cl. ..................... 623/1.35; 623/1.11; 623/903; 623/1.23
(58) Field of Search .............................. 623/1.35–1.37, 623/1.16, 903, 1.11, 1.23

(56) References Cited

U.S. PATENT DOCUMENTS 5,632,763 A    5/1967    Glastra

| 4,577,631 A | 3/1986 | Kreamer |
| 4,733,665 A | 3/1988 | Palmaz |
| 4,795,465 A | 1/1989 | Marten |
| 4,994,071 A | 2/1991 | MacGregor |
| 5,219,355 A | 6/1993 | Parodi et al. |
| 5,316,023 A | 5/1994 | Palmaz et al. |
| 5,383,892 A | 1/1995 | Cardon et al. |
| 5,464,449 A | 11/1995 | Ryan et al. |
| 5,607,444 A | 3/1997 | Lam |

(List continued on next page.)

FOREIGN PATENT DOCUMENTS

| AU | AU-A-37832/95 | 5/1996 |
| DE | 297 01 758 | 5/1997 |
| EP | 0 551 179 | 7/1993 |
| EP | 0 686 379 | 2/1995 |
| EP | 0804 907 | 11/1997 |

(List continued on next page.)

Primary Examiner—David H. Willse
Assistant Examiner—Suzette J. Jackson
(74) Attorney, Agent, or Firm—Kenyon & Kenyon (57) ABSTRACT

A first balloon catheter having a tip extends through the stem portion and first leg portion of a first expandable tubular member and a second balloon catheter having a tip through said stem portion and extends out of a branch aperture such that its tip is longer than that of the first balloon catheter. The first, expandable tubular member, first balloon catheter and second balloon catheter are delivered to a bifurcated vessel having a first lumen and a second lumen with the tip of the second balloon catheter leading the rest of the elements so that the tip of said second balloon catheter can be aligned with and enter into the second lumen before the first expandable tubular member and the tip of said first balloon catheter reach the area of said second lumen and interfere with the second balloon catheter.

17 Claims, 8 Drawing Sheets

U.S. PATENT DOCUMENTS

| | | | |
|---|---|---|---|
| 5,609,605 A | | 3/1997 | Marshall et al. |
| 5,609,627 A | | 3/1997 | Goiocoechea et al. |
| 5,613,980 A | | 3/1997 | Chauhan |
| 5,617,878 A | | 4/1997 | Taheri |
| 5,669,924 A | * | 9/1997 | Shaknovich ............... 623/1.11 |
| 5,749,375 A | | 5/1998 | Maginot |
| 5,755,734 A | * | 5/1998 | Richter et al. ............... 606/194 |
| 5,755,735 A | * | 5/1998 | Richter et al. ............... 606/194 |
| 5,824,052 A | | 10/1998 | Khosravi et al. |
| 5,827,320 A | * | 10/1998 | Richter et al. ............... 606/194 |
| 5,833,707 A | | 11/1998 | McIntyre et al. |
| 5,843,160 A | | 12/1998 | Rhodes |
| 5,906,640 A | | 5/1999 | Penn et al. |
| 5,906,641 A | | 5/1999 | Thompson et al. |
| 5,916,263 A | | 6/1999 | Goicoechea et al. |
| 5,972,017 A | | 10/1999 | Berg |
| 6,033,434 A | | 3/2000 | Borghi |
| 6,056,775 A | * | 5/2000 | Borghi et al. ............... 623/1.16 |
| 6,090,133 A | * | 7/2000 | Richter et al. ............. 623/1.35 |
| 6,096,073 A | | 8/2000 | Webster et al. |
| 6,102,938 A | * | 8/2000 | Evans et al. ............... 623/1.35 |
| 6,117,117 A | * | 9/2000 | Mauch ....................... 604/284 |
| 6,129,738 A | * | 10/2000 | Lashinski et al. ........... 606/194 |
| 6,142,973 A | * | 11/2000 | Carleton et al. ......... 604/96.01 |
| 6,149,682 A | | 11/2000 | Frid |
| 6,162,243 A | | 12/2000 | Gray et al. |
| 6,165,195 A | | 12/2000 | Wilson et al. |
| 6,251,133 B1 | * | 6/2001 | Richter et al. ............. 623/1.16 |
| 6,258,116 B1 | * | 7/2001 | Hojeibane ................... 623/1.16 |
| 6,290,673 B1 | * | 9/2001 | Shanley .................. 604/102.02 |
| 6,325,826 B1 | * | 12/2001 | Vardi et al. ................. 623/1.35 |
| 6,440,165 B1 | * | 8/2002 | Richter et al. ............. 623/1.35 |
| 6,520,987 B1 | * | 2/2003 | Plante ........................ 623/1.16 |
| 6,520,988 B1 | * | 2/2003 | Colombo et al. ........... 623/1.35 |
| 6,540,779 B2 | * | 4/2003 | Richter et al. ............. 623/1.35 |
| 6,599,316 B2 | * | 7/2003 | Vardi et al. ................. 623/1.15 |

FOREIGN PATENT DOCUMENTS

| | | |
|---|---|---|
| EP | 0 943 303 A2 | 3/1999 |
| EP | 0 916 317 A1 | 5/1999 |
| FR | 2 678 508 | 1/1993 |
| WO | WO 95/21592 | 8/1995 |
| WO | WO 96/34580 | 11/1996 |
| WO | WO 96/41592 | 12/1996 |
| WO | WO 97/33532 | 3/1997 |
| WO | WO 98/19628 | 10/1997 |
| WO | WO 97/46174 | 12/1997 |
| WO | WO 98/36708 | 8/1998 |
| WO | WO 00/44307 | 8/2000 |

* cited by examiner

METHOD OF DELIVERING A BIFURCATED STENT

CROSS-REFERENCE TO RELATED APPLICATION

This application is a continuation-in-part of application Ser. No. 09/891,767, filed Jun. 26, 2001 now U.S. Pat. No. 6,540,779, which is a continuation of application Ser. No. 09/072,846, filed May 5, 1998, now Pat. No. 6,251,133, which is a continuation of application Ser. No. 09/049,842, filed Mar. 27, 1998, now Pat. No. 6,090,133, which is continuation of application Ser. No. 08/911,606, filed on Aug. 14, 1997, now Pat. No. 5,827,320, which is a continuation of application Ser. No. 08/841,702, filed on Apr. 30, 1997, now Pat. No. 5,755,735, which is a continuation of application Ser. No. 08/840,612, filed on Apr. 29, 1997, now U.S. Pat. No. 5,755,734, which is a division of application Ser. No. 08/642,297, filed May 3, 1996, now abandoned. This application is also a continuation-in-part of application Ser. No. 10/066,755, filed Feb. 6, 2002, which is a division of Ser. No. 09/575,957, filed May 23, 2001 now U.S. Pat. No. 6,440,165.

FIELD OF THE INVENTION

The present invention relates to stents, and more particularly methods of delivering a bifurcated stent.

BACKGROUND OF THE INVENTION

Stents are well known in the art. They are typically formed of a cylindrical metal mesh, which can expand when pressure is internally applied. Alternatively, they can be formed of wire wrapped into a cylindrical shape or sheets of material formed into a cylindrical shape.

Stents are devices that are usually implanted within bodily conduits including the vascular system to reinforce collapsing, partially occluded, weakened, or abnormally dilated sections of the blood vessel. Stents also have been successfully implanted in other areas, e.g., the urinary tract or the bile duct to reinforce such bodily conduits.

U.S. Pat. No. 4,994,071 (MacGregor) discloses an expandable, bifurcating stent having a main cylindrical lattice formed from interconnected, flexible wire. Two additional cylindrical lattices, having smaller diameters than the main lattice, are similarly constructed. The main lattice includes a flexible wire interconnecting the main lattice to one of the additional lattices. A second flexible wire interconnects the main lattice to the other additional lattice. The flexible wires form backbones that extend axially along the length of the main lattice and along each of the additional lattices. One disadvantage of this bifurcating stent is the complex nature of the interconnection of the flexible wires forming the backbones with the loop structure of each lattice.

Thus, embodiments described in the aforementioned U.S. Pat. No. 6,251,133 provide methods of making a stent which includes a first tubular member having a branch aperture. The tubular member may be inserted in a blood vessel, for example, with the branch aperture aligned with a side branch vessel. A second tubular member having a longitudinal bore may then be disposed and secured within the branch aperture of the first tubular member and, for example, extending into the branch vessel, with the longitudinal bore of the second tubular member in fluid communication with the longitudinal bore of the first tubular member.

One delivery method of a bifurcated stent, such as the stents disclosed in U.S. Pat. No. 6,251,133, to the target area includes mounting the stent on two expandable balloons of the same length. Both expandable balloons are advanced toward the target site together, or are advanced individually in sequential order. One expandable balloon is to be disposed in the main vessel, and one the other is to be disposed in the side branch lumen of the bifurcated vessel. Typically, the side branch balloon is the same length or shorter than the main vessel balloon. Upon reaching the target area in the vessel, the main vessel becomes very crowded due to both balloons filling up the lumen of the main vessel. This causes the tip of the side branch balloon to be pressed against the main vessel, and causes difficulty in orienting the balloon into the side branch lumen, and hinders the ability of the side branch balloon to bend into the side branch vessel.

SUMMARY OF THE INVENTION

Embodiments of the present invention solves these and other disadvantages of the prior art by providing a side branch balloon catheter whose tip leads the tip of the main vessel balloon catheter by few millimeters, so that the side branch balloon leads the delivery system while advancing towards the target area. The side branch balloon catheter reaches the target area first, allowing for greater freedom of the side branch balloon to bend into the aperture of the side branch vessel, due to less crowding of balloon catheter in the main vessel.

DETAILED DESCRIPTION

Figure 1:
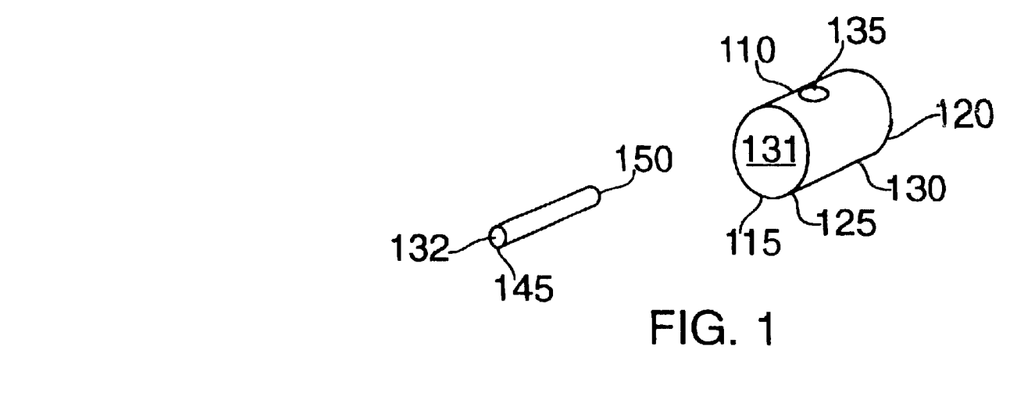
FIG. 1 shows a stem and first leg portion and a second leg portion used to form an embodiment of a bifurcated stent manufactured in accordance with this invention.

FIG. 1 is a general representation of one type of a stent with which the present invention may be used. The stent comprises two portions, which are deployed serially in two steps and assembled within the patient to form a bifurcated stent. FIG. 1 shows stem and first leg portion 110 provided with a longitudinal bore 131 and having a proximal end 115 defining a stem portion 125 and a distal end 120. Second leg portion 140 is provided with a longitudinal bore 132 and has a proximal end 145 and a distal end 150. Stem and first leg portion 110 and second leg portion 140 may be sized and patterned or etched as previously discussed. A branch aperture 135 is disposed between the proximal end 115 and the distal end 120 of stem and first leg portion 110. The branch aperture 135 is sized to receive second leg portion 140 and is adapted to engage and secure the second leg portion 140 when it has been expanded within the branch aperture 135. Second leg portion 140 is sized and adapted to engage and be secured into branch aperture 135 upon expansion.

Figure 2:
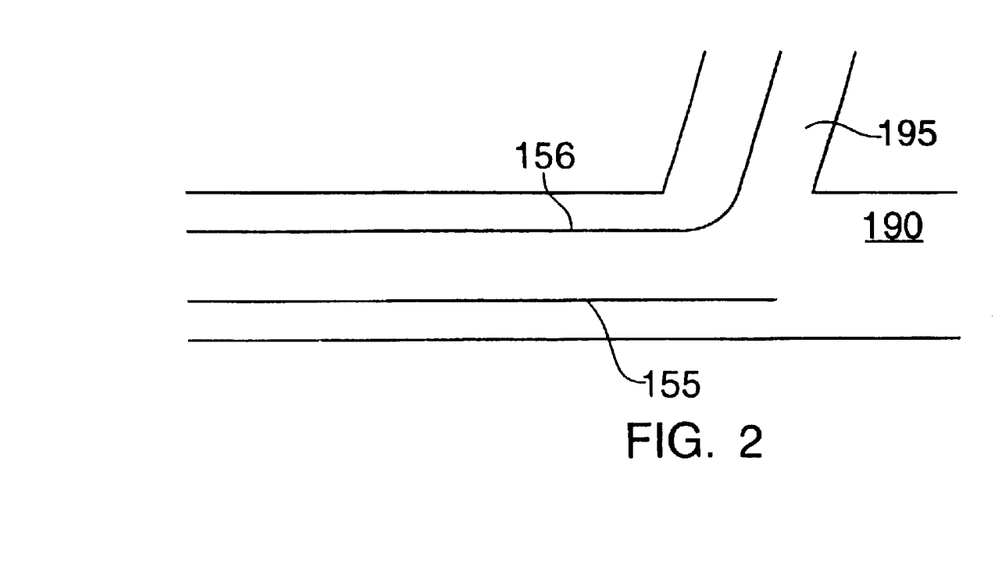
FIG. 2 shows guide wires disposed in the trunk lumen and branch lumen to be treated.

FIGS. 2 to 9 show how the bifurcated stent is assembled within a bifurcated lumen. As shown in FIGS. 2 to 9, the area to be treated is a bifurcated lumen having a first or trunk lumen 190 and a second or branch lumen 195. As shown in FIG. 2, a first guide wire 155 is introduced into the main lumen 190 and a second guide wire 156 is introduced into the branch lumen 195.

Figure 3:
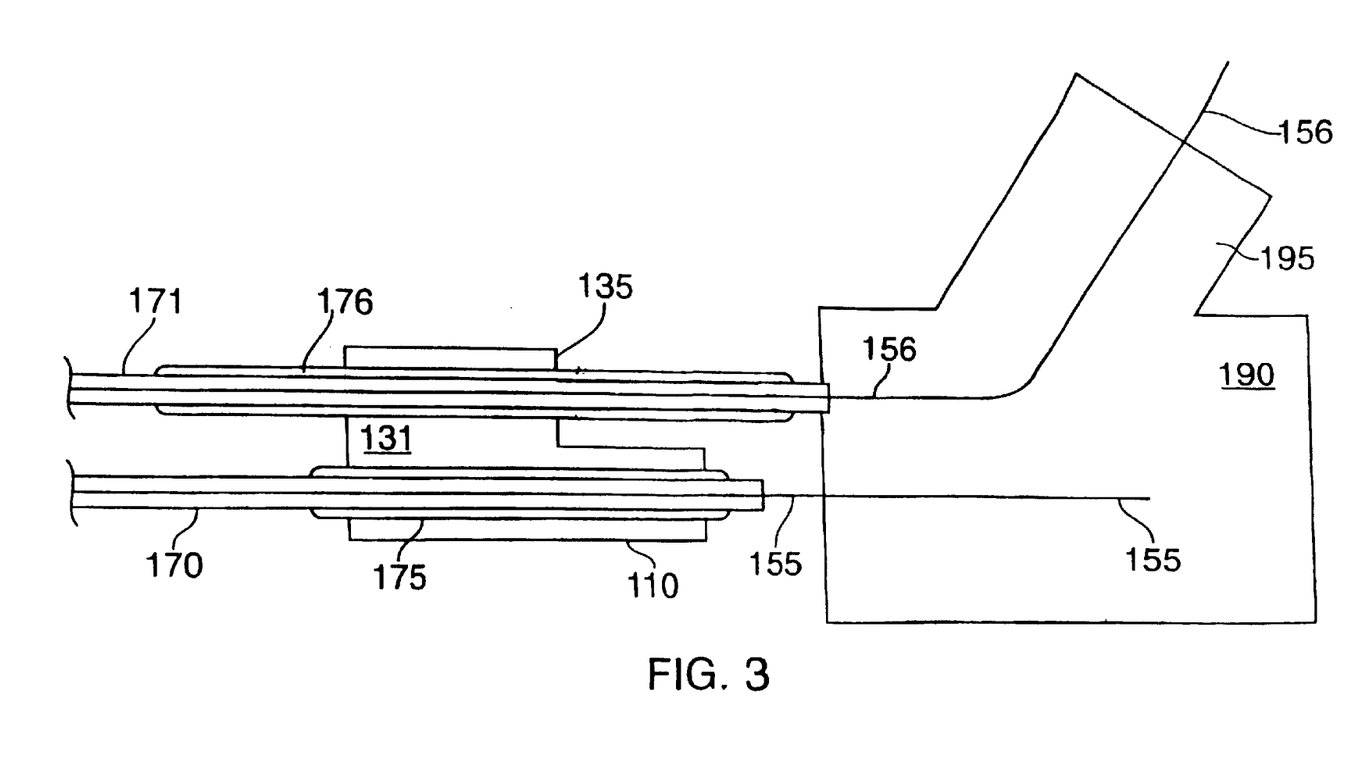
FIG. 3 shows the stem and first leg portion shown in FIG. 1 disposed on catheters and guide wires prior to introduction into the lumen to be treated.

As shown in FIG. 3, a balloon expandable stem and first leg portion 110 of a bifurcated stent is disposed on the tip of a first balloon catheter 170 so that the balloon 175 is disposed within a longitudinal bore 131. A second balloon catheter 171 is then introduced into longitudinal bore 131 of stem and first leg portion 110 and is advanced so that the balloon 176 is disposed within aperture 135, with its tip extending further forward than the tip of the first balloon catheter 170. As illustrated, the tip of balloon 176 leads the whole system. First catheter 170 is then mounted on first guide wire 155 and second catheter 171 is mounted on second guide wire 156. The balloon lengths are selected in conventional fashion; the balloon 176 may be shorter or longer than the balloon 175, so long as its tip is positioned so as to lead.

Figure 4:
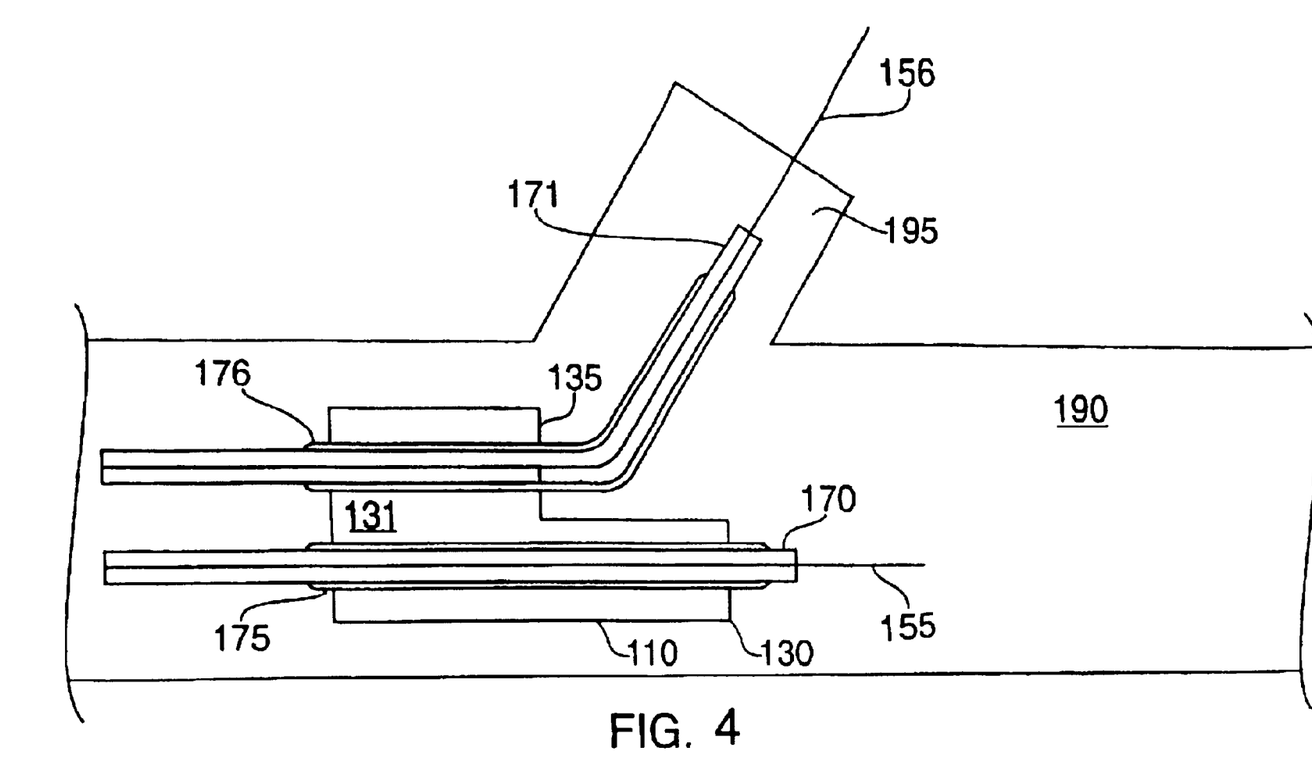
FIG. 4 shows the stem and first leg portion shown in FIG. 1 after it has been delivered to the bifurcation to be treated and prior to its expansion.

As shown in FIG. 4, the unexpanded stem and first leg portion 110 is guided to the area to be treated so that first leg portion 130 is disposed within trunk lumen 190 and branch aperture 135 communicates with branch lumen 195. Because the tip of balloon catheter leads the whole system, it is able to get into the side branch 195 before the rest of the system reaches the area. This greatly facilitates entry of the catheter into, and alignment of the branch aperture 135 with, the side branch 195.

Figure 5:
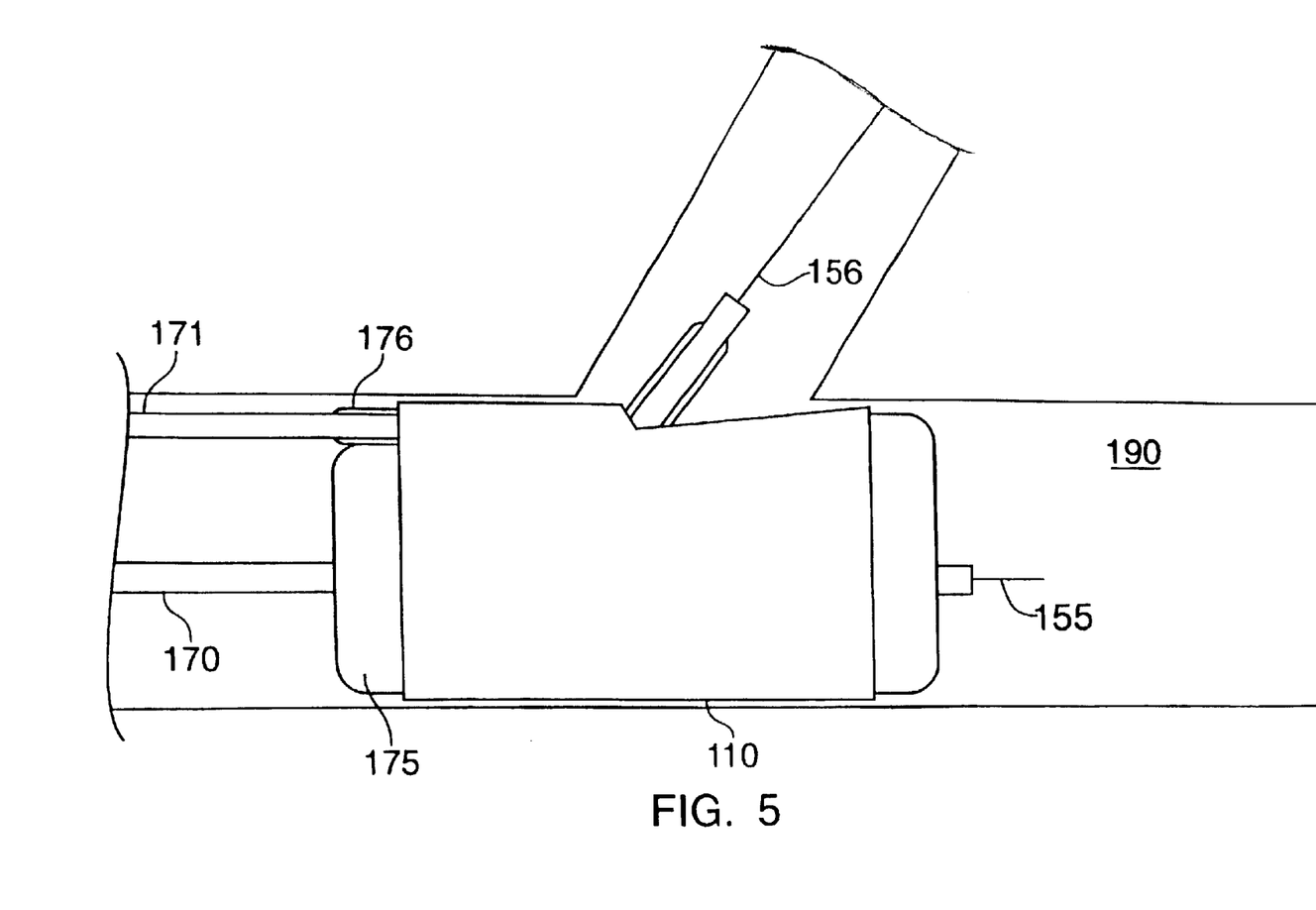
FIG. 5 shows the second leg portion shown in FIG. 4 after it has been expanded.
Figure 6:
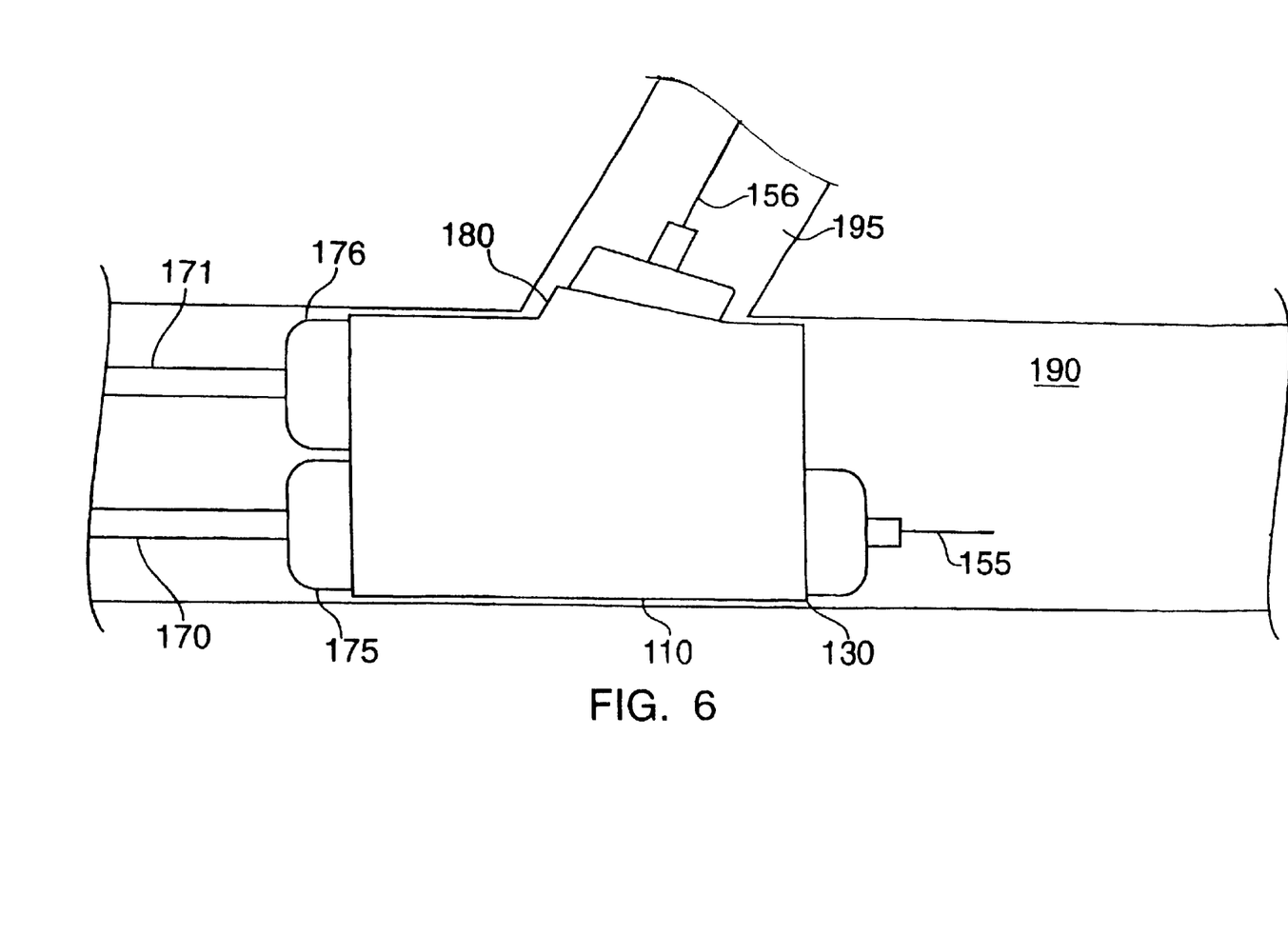
FIG. 6 shows expansion of the branch aperture.

Guide wire 156 facilitates the orientation of the branch aperture 135 with the branch lumen 195. The size of the conventional catheters and balloons is not to scale and details well known to those skilled in the art have been omitted for clarity. In one embodiment, balloon 175 is inflated which causes the stem and first leg portion 110 to expand, as shown in FIG. 5, to secure it in the desired position. After expansion, the external wall of stem and first leg portion 110 would contact the interior walls of trunk lumen 190; however, a gap has been intentionally left for clarity. The balloon 175 on first catheter 170 is left inflated and the balloon 176 on second catheter 171 is then inflated to enlarge the branch aperture 135 as shown in FIG. 6. As the branch aperture 135 is enlarged a portion of the stent defining the branch aperture 135 is pushed outward to form a branch securing lip 180.

Figure 7:
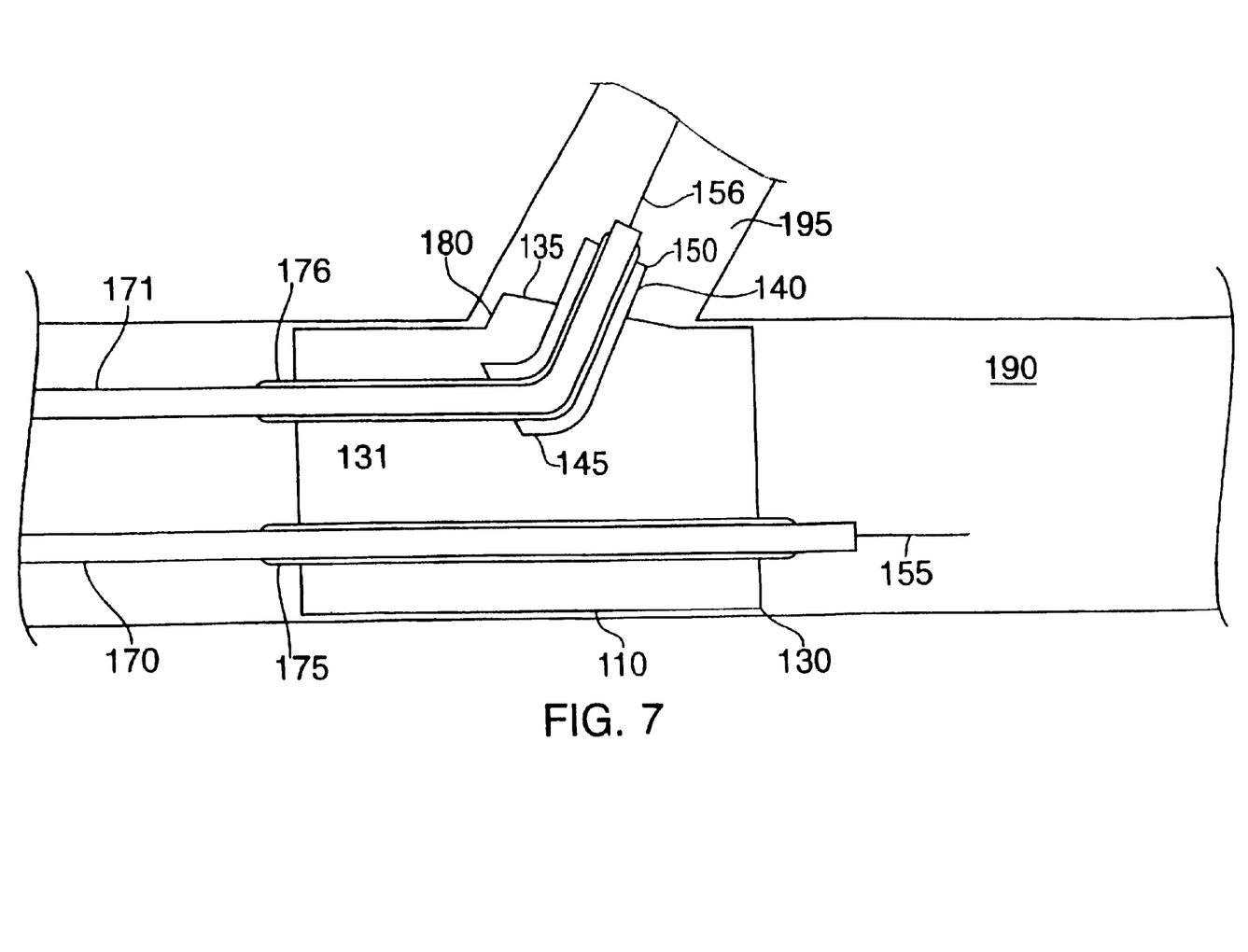
FIG. 7 shows the unexpanded second leg portion disposed in the branch aperture.

In this embodiment, balloons 175 and 176 are deflated, second catheter 171 is withdrawn, and second guide wire 156 is left in place in the branch lumen 195. Second leg portion 140 is then applied to second catheter 171 so that balloon 176 is disposed in longitudinal bore 132 and second catheter 171 is then applied to second guide wire 156. Second leg portion 140 is then guided to, and introduced into, the longitudinal bore 131 of the stem and first leg portion 110 and is advanced and passed through branch aperture 135 so that the distal end 150 of the second leg portion 140 protrudes into the branch lumen 195 and the proximal end 145 communicates with longitudinal bore 131, as shown in FIG. 7. The balloon 176 on second catheter 171 is partially inflated and the balloon 175 on first catheter 170 is then partially inflated to a pressure substantially equal to the pressure in balloon 176. Both balloons 175 and 176 are then simultaneously inflated to substantially equal pressures.

Figure 8:
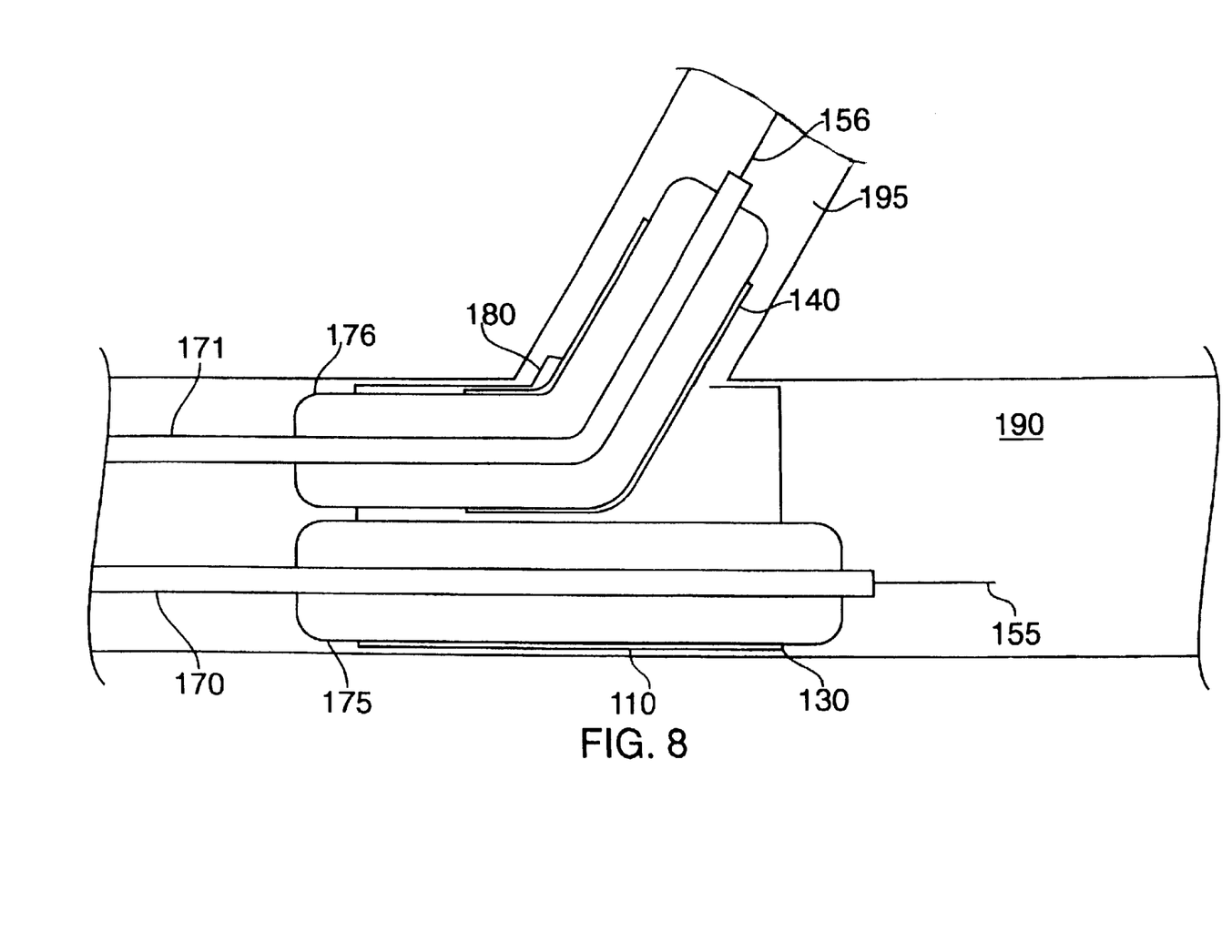
FIG. 8 shows the expansion of the second leg portion shown in FIG. 7.
Figure 9:
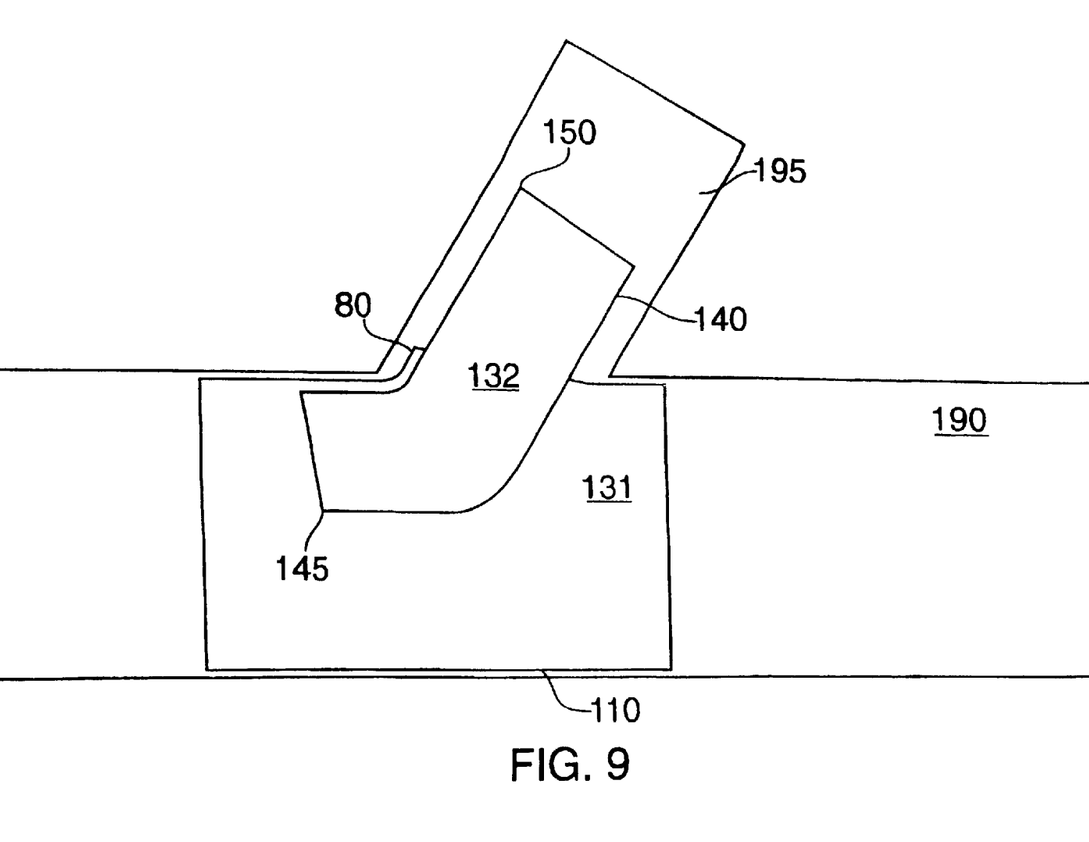
FIG. 9 shows the assembled bifurcated stent disposed in the bifurcated lumen to be treated.

As shown in FIG. 8, inflation of the balloon 176 on second catheter 171 causes second leg member 140 to expand so that its external walls engage and are secured to the area surrounding aperture 135. Inflation of the balloon 175 on the first catheter 170 prevents stem and first leg portion 110 from collapsing when balloon 176 is inflated. After expansion, the external walls of second leg 140 would contact the inner wall of lumen 195; however, a gap has been intentionally left for clarity. The balloons 175 and 176 are deflated, catheters 170 and 171 and guide wires 155 and 156 are withdrawn, and the assembled bifurcated stent 160 is left in place as shown in FIG. 9.

An alternative embodiment of a method of making a bifurcated stent comprises the steps of preparing a first expandable tubular member 110 having a proximal end 115 and a distal end 120 and a longitudinal bore 131 therethrough. The first tubular member 110 is provided with a branch aperture 135 disposed between the proximal end 115 and the distal end 120. The branch aperture 135 communicates with the longitudinal bore 131 of the first expandable tubular member 110 and the aperture 135 is sized and adapted to receive and secure a second expandable tubular member 140. The first expandable tubular member 110 is delivered to a bifurcated vessel having a first lumen 190 and a second lumen 195 so that the first expandable tubular member 110 is disposed within the first lumen 190 and the branch aperture 135 communicates with the second lumen 195. The branch aperture 135 is aligned with the second lumen 195 and may be widened by first inflating the balloon 176 of FIG. 4. As specific applications dictate, the portion of the first expandable tubular member defining the branch aperture 135 may be adapted to form a branch securing lip when the branch aperture 135 is expanded a sufficient amount by inflating the balloon 176.

As shown in FIG. 5, the first expandable tubular member 110 is then expanded an amount sufficient to secure the first expandable tubular member 110 in the first lumen 190. A second expandable tubular member 140 is prepared having a proximal end 145 and a distal end 150 having longitudinal bore 132 therethrough. The second expandable tubular member 140 is delivered into the branch aperture 135 so that the distal end 150 of the second expandable tubular member 140 is disposed within the second lumen 195 and the proximal end 145 of the second expandable tubular member 140 is disposed within the branch aperture 135 of the first tubular member 110 and so that the longitudinal bore 132 of the second expandable tubular member 140 is in fluid communication with the longitudinal bore 131 of the first longitudinal tubular member 110. As shown in FIG. 6, the second expandable tubular member 140 is then expanded in an amount sufficient to secure the second expandable tubular member 140 within the second lumen 195 and within the branch aperture 135 of the first expandable tubular member 110.

In one particular embodiment, a first guide wire 155 is delivered into the first lumen 190 of a bifurcated vessel having a first lumen 190 and a second lumen 195 and a second guide wire 156 is delivered into the second lumen 195 of the bifurcated vessel. A first expandable tubular member 110 is prepared having a proximal end 115 and a distal end 120 and a longitudinal bore 131 therethrough. The first expandable tubular member 110 is provided with a branch aperture 135 disposed between the proximal end 115 and the distal end 120. The branch aperture 135 communicates with the longitudinal bore 131 and the branch aperture 135 is sized and adapted to receive and secure a second expandable tubular member 140. The first expandable tubular member 110 is mounted on a first balloon catheter 170 and the first balloon catheter 170 is mounted on the first guide wire 155.

The first expandable tubular member 110 is delivered to the first lumen 190 of the bifurcated vessel so that the first expandable tubular member 110 is disposed within the first lumen 190 and the branch aperture communicates 135 with the second lumen 195. A second balloon catheter 171 is mounted on the second guide wire 156 and the balloon portion 176 of the second balloon catheter 171 is delivered into the side-branch aperture 135. In accordance with the present invention, both balloons may be inserted through the stem portion of the tubular member and delivered to the bifurcated vessel simultaneously. As explained previously, the tip of balloon catheter 171 leads the whole system, permitting it to be more easily aligned with and inserted in the branch lumen 195.

The second balloon catheter 171 is inflated to align the branch aperture 135 with the second lumen 195. It may additionally be inflated sufficiently to widen the branch aperture 135. The first balloon catheter 170 may then be inflated to expand the first expandable member 110 in an amount sufficient to secure the first expandable member 110 in the first lumen 190. The first 170 and second 171 balloon catheters are deflated and the second balloon catheter 171 is removed.

A second expandable tubular member 140 is prepared having a proximal end 145 and a distal end 150 having longitudinal bore 132 therethrough. The second expandable tubular member 140 is mounted on the second balloon catheter 171. The second expandable tubular member 140, mounted on the second balloon catheter 171, is delivered into the branch aperture 135 so that the distal end 150 of the second expandable tubular member 140 is disposed within the second lumen 195 and the proximal end 145 of the second expandable tubular member 140 is disposed within the branch aperture 135 of the first tubular member 110 and so that the longitudinal bore 132 of the second expandable tubular member 140 is in fluid communication with the longitudinal bore 131 of the first longitudinal member 110. The first balloon catheter 170 may be inflated. The second balloon catheter 171 is inflated to expand the second expandable tubular member 140 in an amount sufficient to secure the second expandable tubular member 140 within the second lumen 195 and within the branch aperture 135.

As specific applications dictate, the portion of the first tubular stent 110 defining the side branch aperture 135 may be adapted to form a branch securing lip when the branch aperture 135 is expanded a sufficient amount. In one embodiment, the first balloon catheter 170 is inflated before the second balloon catheter 171 is inflated and the first balloon catheter 170 is left inflated until the second expandable tubular member 140 is secured within the branch aperture 135 by the second balloon catheter 171. In another embodiment, the first balloon catheter 170 and the second balloon catheter 171 are inflated simultaneously.

The stent with which the methods of the present invention may be used can be of any construction that provides first expandable tubular member 110 having a proximal end 115 and a distal end 120 and a longitudinal bore 131 therethrough, with a branch aperture 135 disposed between the proximal end 115 and the distal end 120 communicating with the longitudinal bore 131 of the first expandable tubular member 110 and aperture 135 is sized and adapted to receive and secure a second expandable tubular member 140. Exemplary embodiments of structures which meet this requirement and the method of making them are disclosed in U.S. application Ser. No. 09/575,957, particularly in FIGS. 22 to 34. The disclosure of Ser. No. 09/575,957 is hereby incorporated by reference in its entirety.

What is claimed is:

1. A method comprising:
   a) inserting a first balloon catheter having a tip through a first expandable tubular member having a proximal end forming a stem portion and a distal end forming a first leg portion and a longitudinal bore therethrough such that it extends through said stem portion and first leg portion, the first tubular member provided with a branch aperture disposed between the proximal end and the distal end;
   b) inserting a second balloon catheter having a tip through said stem portion and extending out of said branch aperture such that its tip is longer than that of the first balloon catheter.

2. The method according to claim 1 and further including:
   c) delivering the first expandable tubular member, first balloon catheter and second balloon catheter to a bifurcated vessel having a first lumen and a second lumen with the tip of said second balloon catheter leading the rest of the elements.

3. The method according to claim 2 and further including:
   d) leading said tip of said second balloon catheter into the second lumen before said first expandable tubular member and said tip of said first balloon catheter reach the area of said second lumen.

4. The method according to claim 3 and further including:
   e) disposing the first expandable member within the first lumen.

5. The method according to claim 4 and further including:
   f) inflating said second balloon.

6. The method according to claim 5 wherein said inflating widens the branch aperture in an amount sufficient to further align the branch aperture with the second lumen.

7. The method according to claim 5 and further including:
   g) expanding the first expandable member in an amount sufficient to secure the first expandable member in the first lumen.

8. The method according to claim 7 and further including:
   h) preparing a second expandable tubular member having a proximal end and a distal end having longitudinal bore therethrough;
   i) delivering the second expandable tubular member into the branch aperture so that the distal end of the second expandable tubular member is disposed within the second lumen and the proximal end of the second expandable tubular member is disposed within the branch aperture of the first tubular member, the longitudinal bore of the second expandable tubular member in fluid communication with the longitudinal bore of the first longitudinal member; and
   j) expanding the second expandable tubular member in an amount sufficient to secure the second expandable tubular member within the second lumen and within the branch aperture.

9. The method of claim 5, wherein during step f) the branch aperture is widened in an amount sufficient to form a branch securing lip.

10. A method comprising:
    a) delivering a first guide wire into the first lumen of a bifurcated vessel having a first lumen and a second lumen;

b) delivering a second guide wire into the second lumen of the bifurcated vessel;

c) mounting a first expandable tubular member having a proximal end forming a stem portion and a distal end forming a first leg portion and a longitudinal bore therethrough on a first balloon catheter having a tip, the first tubular member provided with a branch aperture disposed between the proximal end and the distal end, the branch aperture communicating with the longitudinal bore;

d) mounting the first expandable tubular member on a second balloon catheter having a tip, with the balloon catheter extending out of the branch aperture such that its tip is longer than the tip of the first balloon catheter;

e) mounting the first balloon catheter on the first guide wire and the second balloon catheter on the second guide wire;

f) delivering the first expandable tubular member to the first lumen of the bifurcated vessel with the tip of the second balloon catheter leading the rest of the elements and entering into the second lumen first followed by the first expandable member entering into the first lumen;

g) inflating the second balloon catheter; and h) inflating the first balloon catheter to expand the first expandable member in an amount sufficient to secure the first expandable member in the first lumen.

11. The method according to claim 10 and further including:

a) removing the second balloon catheter;

b) mounting a second expandable tubular member having a proximal end and a distal end having longitudinal bore therethrough on the second balloon catheter;

c) delivering the second expandable tubular member into the branch aperture so that the distal end of the second expandable tubular member is disposed within the second lumen and the proximal end of the second expandable tubular member is disposed within the branch aperture of the first tubular member, the longitudinal bore of the second expandable tubular member in fluid communication with the longitudinal bore of the first longitudinal member; and d) inflating the second balloon catheter to expand the second expandable tubular member in an amount sufficient to secure the second expandable tubular member within the second lumen and within the branch aperture.

12. The method according to claim 11 and further including:

a) deflating the first and the second balloon catheters;

b) removing the second balloon catheter;

c) mounting a second expandable tubular member having a proximal end and a distal end having longitudinal bore therethrough on the second balloon catheter;

d) delivering the second expandable tubular member into the branch aperture so that the distal end of the second expandable tubular member is disposed within the second lumen and the proximal end of the second expandable tubular member is disposed within the branch aperture of the first tubular member, the longitudinal bore of the second expandable tubular member in fluid communication with the longitudinal bore of the first longitudinal member;

e) inflating the first balloon catheter; and f) inflating the second balloon catheter to expand the second expandable tubular member in an amount sufficient to secure the second expandable tubular member within the second lumen and within the branch aperture.

13. The method of claim 11, wherein the branch aperture is widened in an amount sufficient to form a branch securing lip.

14. The method of claim 12, wherein, the second expandable tubular member is widened in an amount sufficient to form a branch securing lip.

15. The method of claim 10, wherein the first balloon catheter is inflated before the second balloon catheter is inflated and the first balloon catheter is left inflated until the second expandable tubular member is secured within the branch aperture by the second balloon catheter.

16. Apparatus comprising:

a) first expandable tubular member having a proximal end forming a stem portion and a distal end forming a first leg portion and a longitudinal bore therethrough, the first tubular member provided with a branch aperture disposed between the proximal end and the distal end;

b) a first balloon catheter having a tip extending through said stem portion and first leg portion; and c) a second balloon catheter having a tip extending through said stem portion and extending out of said branch aperture such that its tip is longer than that of the first balloon catheter.

17. Apparatus according to claim 16 and further including:

d) a second expandable tubular member having a proximal end and a distal end having longitudinal bore therethrough and having a diameter permitting the proximal end of the second expandable tubular member, when expanded to be securely disposed within the branch aperture of the first tubular member, the longitudinal bore of the second expandable tubular member in fluid communication with the longitudinal bore of the first longitudinal member.

* * * * *